United States Patent [19]

Murthy et al.

[11] Patent Number: 4,830,853

[45] Date of Patent: May 16, 1989

[54] DRUG COMPOSITIONS STABILIZED AGAINST OXIDATION

[75] Inventors: Kuchi S. Murthy, Morris Plains; Michael R. Harris, Hackettstown; Gerard C. Hokanson, Long Valley; Robert G. Reisch, Jr., Haledon; Mahdi B. Fawzi, Flanders; Frank Waldman, Wayne, all of N.J.

[73] Assignee: Warner-Lambert Company, Morris Plains, N.J.

[21] Appl. No.: 921,717

[22] Filed: Oct. 20, 1986

[51] Int. Cl.$^4$ ................................................. A61K 9/68
[52] U.S. Cl. .................................... 424/440; 424/464; 424/468

[58] Field of Search ............... 424/440, 464, 465, 468, 424/476, 482

[56] References Cited

U.S. PATENT DOCUMENTS

| | | | |
|---|---|---|---|
| 3,697,641 | 10/1972 | Ahrens | 426/72 X |
| 4,656,188 | 4/1987 | Veber et al. | 514/310 X |
| 4,666,705 | 5/1987 | DeCrosta et al. | 424/470 X |

Primary Examiner—Michael Lusignan
Attorney, Agent, or Firm—Howard Olevsky; Ronald A. Daignault

[57] ABSTRACT

The oxidation—and color-stability of certain ace inhibitors is optimized when they are formulated with a stabilizer and at least one lubricant and/or excipient.

21 Claims, No Drawings

DRUG COMPOSITIONS STABILIZED AGAINST OXIDATION

BACKGROUND

Certain Angiotensin Converting Enzyme (ACE) inhibitors are highly susceptible to oxidative attack resulting in discoloration when they are formulated into pharmaceutical dosage forms. It is the conversion to unwanted colored substances which can lessen drug effectiveness in compositions containing this type of drug.

THE INVENTION

It has been discovered that discoloration and degradation due to oxidation which have been common problems associated with dosage forms containing, e.g., quinapril, can be overcome via the use of ascorbic acid and/or sodium ascorbate as ingredient(s) in the formulation.

The effect of the ascorbic acid is maximized when certain lubricants, e.g., Sterotex®, and/or talc, are used in combination therewith. Furthermore, the overall stability of the final pharmaceutical formulation is enhanced when specific types of excipients, such as mannitol and lactose are included therein.

ADVANTAGES

The compositions of the invention have several advantages over compositions which do not contain the stabilizing additive(s) discussed herein. Principally, the active ingredients or drug contained therein is initially preserved from oxidative attack.

Furthermore, the discoloration which sometimes occurs when ACE inhibitors of this class are formulated and allowed to stand for significant periods of time, is minimized or eliminated completely. Thus, tabletted quinapril formulations can be produced which will undergo no detectable discoloration due to oxidation.

In addition to their greater storage stability, the formulations of the invention are rendered more suitable for use in drug combinations.

These and other advantages of the invention will become apparent from a consideration of the following description of the invention.

DESCRIPTION OF THE INVENTION

The invention deals with:

I. A pharmaceutical composition which contains:
(a) a drug component which comprises an ACE inhibitor which is susceptible to oxidation and discoloration,
(b) an amount of ascorbic acid, sodium ascorbate or mixture thereof suitable to inhibit oxidation and, optionally,
(c) one or more components which do not significantly interfere in the function of component (b).

II. A process for stabilizing an ACE inhibitor drug which comprises the steps of contacting the drug with:
(a) an amount of ascorbic acid, sodium ascorbate or mixture thereof to inhibit oxidation, and, optionally,
(b) one or more compounds which do not significantly interfere with the function of (a).

III. A method of making a pharmaceutical dosage form which comprises the step of including in the formulation suitable amounts of:
(a) an ACE inhibitor,
(b) one or more of ascorbic acid and sodium ascorbate as an oxidation stabilizer, and optionally,
(c) lubricants and/or excipients which do not interfere with the function of (b).

DRUG COMPONENT(S)

The compositions of the invention contain at least one ACE inhibitor and, optionally, one or more other medicament drugs or beneficial substances.

The ACE inhibitors which can be used in the invention are any of a number of well-known compounds which have antihypertensive properties.

One preferred group of compounds includes those of the general formula:

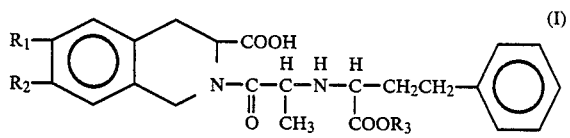

wherein $R_1$ and $R_2$ are —H or —$OC_nH_{2n+1}$; $R_3$ is —H or $C_nH_{2n+1}$, and n = 1–5. Preferably, $R_1$ and $R_2$ are the same. Most preferably, $R_1$ and $R_2$ are both $CH_3O$— or H— when $R_3$ is —H or —$CH_2H_5$ Mixtures are operable.

The production of compounds of this type is disclosed in U. S. Pat. No. 4,344,949, the disclosure of which is hereby incorporated by reference.

One preferred ACE inhibitor is Quinapril. It has the structure:

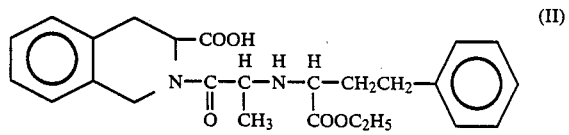

The drug component(s) of the instant compositions can contain pharmaceutically acceptable analogs, e.g., salts, of the drugs discussed herein in place of all or part of the drug named.

Enalapril and structurally related compounds are another preferred group of drugs. These drugs have structures which conform to formula (III)

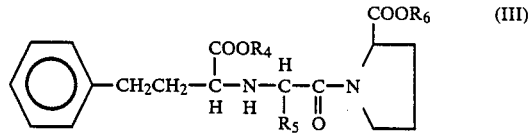

wherein $R_4$ and $R_5$ are $C_{1-4}$ alkyl, and $R_6$ is H or $C_{1-4}$ alkyl.

The total drug content of the final composition will be from about 2 to about 30%, preferably about 3% to about 20%. When one or more ace inhibitor(s) is the only drug present, the total concentration of ace inhibitors in the final dosage form will be about 1% to about 70%, preferably about 2% to about 30%.

All percentages stated herein are weight percentages based on total composition weight, unless otherwise stated.

The daily dosages, of the pharmaceutical preparations to be used depend upon such factors as the nature of the dosage form, the nature of the drug(s) and the type and extent of any interaction(s) in drug combinations. Thus, the therapeutic needs of the individual patient and the desires of the prescribing physician will often dictate the dosage levels to be employed.

In general, however, the manufacturer's specifications for any drug or drug combination are useful guides to administration. The *Physician's Desk Reference* or other competent publication can be consulted to ascertain appropriate dosage levels.

Nonetheless, typical dosage levels for quinapril and enalapril are 2 mg to 80 mg per dosage.

Suitable categories of drugs that may be employed in addition to ace inhibitors in the instant compositions may vary widely and generally represent any stable drug combination.

Illustrative categories and specific examples include:

(a) Antitussives, such as dextromethorphan, dextromethorphan hydrobromide, noscapine, carbetapentane citrate, and chlophedianol hydrochloride;

(b) Antihistamines, such as chlorpheniramine maleate, phenindamine tartrate, pyrilamine maleate, doxylamine succinate, and phenyltoloxamine citrate, (c) Decongestants, such as phenylephrine hydrochloride, phenylpropanolamine hydrochloride, pseudoephedrine, hydrochloride ephedrine; and (d) Various alkaloids, such as codeine phosphate, codeine sulfate and morphine.

(e) Mineral supplements such as potassium chloride and calcium carbonates.

The medicaments and/or other beneficial substances to be used herein may be selected from a wide variety of substances and pharmaceutically acceptable forms thereof, e.g., their acid addition salts. Both organic and inorganic salts may be used provided the drug maintains its medicament value. Exemplary acid salts include hydrochloride, hydrobromide, orthophosphate, benzoate, maleate, tartrate, succinate, citrate, salicylate, sulfate, acetate, and the like. Mixtures are operable.

One preferred group of drugs to be used in combination with ace inhibitors includes beta-blockers, diuretics, calcium blockers, and the like.

Stabilizer(s)

The oxidative instability which is exhibited by some of the drugs discussed above can be overcome via the use of one or more of ascorbic acid and sodium ascorbate as stabilizer(s).

While the use of ascorbic acid as an antioxidant for pharmaceuticals is known, its function as an oxidation inhibitor in stable ACE inhibitor formulations is not yet known. All or part of the ascorbic acid can be replaced with a metal or ammonium ascorbate, e.g., sodium, potassium and/or iodine ascorbate(s). Ascorbic acid and sodium ascorbate are preferred; ascorbic acid itself is highly preferred.

The quantity of ascorbic acid or other ascorbic species, ie., ascorbate salt to be used to stabilize the compositions of the invention will lie between about 0.5% and about 15%, preferably about 1.0% to about 10.0%. In general, any amount which will effectively retard or prevent oxidation and discoloration of the ACE inhibitor component(s) can be used.

The phase "ascorbic acid component" is used herein to mean the acid and/or one or more of the salts discussed above.

Minor amounts of one or more other stabilizers can be tolerated in the instant formulations, but their use must not significantly interfere with the operation of the ascorbic stabilizer which is used.

Lubricant(s)

The optional lubricant component(s) to be used in the pharmaceutical products and methods of the invention are substances which are compatible with the ascorbic acid stabilizer. Generally, they are substances which do not contain groups which could significantly interfere with the function of either the ascorbic component or the drug component.

One preferred group of lubricants include hydrogenated vegetable oils, e.g., hydrogenated cottonseed oil, e.g., sterotex ® and talc. Mixtures are operable.

It is thought that the presence of readily ionizable moieties in the lubricant component adversely affects the action of the ascorbic stabilizer. Thus, stearic acid and conventional metal salts thereof are not operable lubricants in the instant formulations because they interfere with the ability of ascorbic acid to prevent oxidation.

Generally, the quantity of lubricant present will be from about 0.5% to about 10%, preferably about 1% to about 5%.

Excipient(s)

The optional excipients which can be used in the instant compositions are also substances which must be compatible with the ascorbic acid component so when resold, they do not interfere with its function in the composition. Generally, the excipients to be used herein include sugars such as mannitol, lactose, and other sweeteners and carriers which do not adversely affect the function of the other ingredients in the composition. Mannitol, lactose, and other sugars are preferred. Mixtures are operable.

The compositions of the invention may contain carriers, diluents, pigments, binders, colorants, and other additives conventionally used in the production of pharmaceutical products.

The method by which the ingredients are combined—ie., the processing of the products of the invention—is not critical. Any techniques which are appropriate according to the physical and chemical nature of the materials to be treated can be employed.

The percentages in which excipients are used are not critical. In general, their quantities will be consistent with the amount given above for the drug, stabilizer, and lubricant components, ie., they make up the remainder of the composition.

Dosage Forms

The final form of the pharmaceutical preparations made in accordance with the invention can vary greatly. Thus, tablets, capsules, sachets, sprinklers, pomades, transdermal compositions buccal preparations, candy compositions, nasal formulations, ocular compositions, and the like are contemplated. Tablets, caplets, and capsules are preferred.

Solid, semi-solid, and liquid formulations can be made, however, solids are highly preferred.

The drug preparations can be adapted for immediate, slow, or sustained release profiles, or any combination of these. Thus a formulation adapted to give an initial loading dosage within 30 minutes followed by sustained release of the remaining drug over 4 to 12 hours is contemplated. Sustained and immediate release formulations are preferred.

EXAMPLES

A formulation containing the following ingredients was prepared:

| Ingredient | wt % |
|---|---|
| Quinapril | 5 |
| Ascorbic Acid | 20 |
| Lactose | 71 |
| Hydrogenated Vegetable Oil | 4 |
| Total | 100 |

This formulation was stable at 80% relative humidity for at least 24 hours in open containers.

Reasonable variations, such as those which would occur to a skilled artisan, can be made herein without departing from the scope of the invention.

We claim:

1. A pharmaceutical composition which contains:
   (a) an effective amount of a drug component which comprises an ACE inhibitor which is susceptible to discoloration,
   (b) a color stabilizing amount of one or more of ascorbic acid, and, sodum ascorbate at a level of about 0.5% to about 15% by weight of the composition, and, optionally,
   (c) one or more components which do not significantly interfere in the function of component (b).

2. The composition of claim 1 wherein (c) is at least one material selected from the group consisting of: excipients and lubricants.

3. The composition of claim 2 wherein (a) is quinapril and (c) contains a lubricant and an excipient.

4. The composition of claim 3 wherein the lubricant is selected from the group consisting of hydrogenated vegetable oil, talc, and mixtures thereof.

5. The composition of claim 4 wherein the excipient is selected from the group consisting of mannitol and lactose.

6. The composition of claim 5 wherein the lubricant is hydrogenated cottonseed oil.

7. The composition of claim 6 wherein (a) contains at least one additional drug.

8. A tablet containing the composition of claim 6.

9. A tablet containing the composition of claim 7.

10. A candy formulation containing the composition of claim 6.

11. A candy formulation containing the composition of claim 7.

12. A process for stabilizing an ACE inhibitor drug which comprises the step of contacting the drug with:
    (a) from about 0.5% to about 15% of one or more of ascorbic acid, and sodium ascorbate by weight of the combination with the drug and optionally,
    (b) one or more compounds which do not significantly interfere with the function of (a).

13. The process of claim 12 wherein the drug employed is at least one compound which conforms to formula (I)

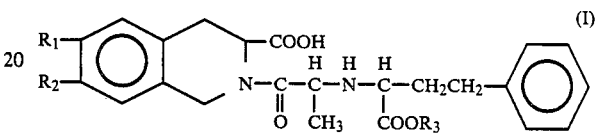

wherein $R_1$ and $R_2$ are —H or —$OC_nH_{2n+1}$; $R_3$ is —H or —$C_nH_{2n+1}$; and n=1 to 5.

14. The process of claim 13 wherein $R_1$, and $R_2$ are —H and $R_3$ is —$CH_2H_5$.

15. The process of claim 13 wherein $R_1$ and $R_2$ are both —$OCH_3$ and $R_3$ is either —H or —$C_2H_5$.

16. The process of claim 12 wherein the drug is enalapril.

17. The process of claim 13 wherein (b) is selected from the group consisting of lubricants, excipients, and mixtures thereof.

18. The process of claim 17 wherein (b) contains a lubricant and an excipient.

19. The method of claim 18 wherein the lubricant is selected from the group consisting of: hydrogenated vegetable oil, talc, and mixtures thereof.

20. The method of claim 19 wherein the excipient is selected from the group consisting of mannitol and lactose.

21. The method of claim 20 wherein the lubricant is hydrogenated cottonseed oil.

* * * * *